United States Patent
Jimenez Cruz et al.

(10) Patent No.: US 10,065,915 B2
(45) Date of Patent: Sep. 4, 2018

(54) USE OF HETEROGENEOUS ACID CATALYSTS BASED ON MIXED METAL SALTS TO PRODUCE BIODIESEL

(71) Applicant: INSTITUTO MEXICANO DEL PETROLEO, Mexico City (MX)

(72) Inventors: Federico Jesus Jimenez Cruz, Mexico City (MX); Celia Marin Rosas, Mexico City (MX); Luis Carlos Castaneda Lopez, Mexico City (MX); Rogelio Hernandez Suarez, Mexico City (MX); Javier Esteban Rodriguez Rodriguez, Mexico City (MX); Maria del Carmen Martinez Guerrero, Mexico City (MX); Florentino Rafael Murrieta Guevara, Mexico City (MX); Alicia del Rayo Jaramillo Jacob, Mexico City (MX)

(73) Assignee: INSTITUTO MEXICANO DEL PETROLEO, Mexico City (MX)

( * ) Notice: Subject to any disclaimer, the term of this patent is extended or adjusted under 35 U.S.C. 154(b) by 0 days.

(21) Appl. No.: 15/474,837

(22) Filed: Mar. 30, 2017

(65) Prior Publication Data
US 2017/0283723 A1    Oct. 5, 2017

(30) Foreign Application Priority Data
Mar. 31, 2016    (MX) .................... MX/a/2016/004133

(51) Int. Cl.
*C07C 67/02*    (2006.01)
*C11C 3/00*    (2006.01)
(Continued)

(52) U.S. Cl.
CPC ............. *C07C 67/02* (2013.01); *B01J 27/053* (2013.01); *B01J 27/055* (2013.01); *B01J 27/16* (2013.01);
(Continued)

(58) Field of Classification Search
CPC ... C11C 3/00; C11C 3/003; C11C 3/10; C07C 67/02; C07C 67/03; B01J 27/053;
(Continued)

(56) References Cited

U.S. PATENT DOCUMENTS 8,039,652 B2 * 10/2011 Portnoff .................. C07C 67/08
554/169
2005/0274065 A1 * 12/2005 Portnoff .................. C07C 67/08
44/605
(Continued)

FOREIGN PATENT DOCUMENTS

EP    1607467 A1 * 12/2005 .............. B01J 23/30

OTHER PUBLICATIONS

Furuta, S., et al., Biodiesel fuel producitn with solid amorphous-zirconia catalysis in fixed bed reactor, 2006, Biomass & Bioenergy, vol. 30, No. 10, pp. 870-873 (Year: 2006).*

*Primary Examiner* — Yate Kai Rene Cutliff
(74) *Attorney, Agent, or Firm* — Dickinson Wright PLLC

(57) ABSTRACT

The present invention relates to the production of biodiesel and alkyl esters by the transesterification of triglyceride esters, with alcohols in heterogeneous phase in the presence of heterogeneous catalysts, with yields higher than 80%, at a temperature from 0 to 300° C., residence time from 20 minutes to 20 h, space velocity of 0.1 to 10 h$^{-1}$, pressure of 25-100 kg/cm$^2$ (24.5-98.07 bar), methanol/oil molar ratio of 10 to 40 and catalyst concentration of 0.001 to 20 weight % based on tri-, di- or monoglyceride. The method produces biodiesel and alkyl esters by transesterification of tri-, di- or
(Continued)

mono-glycerides, from palm, jatropha, castor, soybean and sunflower oils, wherein the alcohoxyls $R^1O$, $R^2O$ and $R^3O$ of the glycerides are $C_1$ to $C_{24}$ and a $C_1$-$C_4$ alcohol, such as methanol, in an alcohol:oil ratio from 3:1 to 50:1. The transesterification reaction produces biodiesel while avoiding loss of catalyst, contaminating liquid effluents and eliminating undesirable hydrolysis of triglycerides, diglycerides and monoglycerides into free fatty acids and saponification that generate soaps.

21 Claims, 5 Drawing Sheets

(51) Int. Cl.
| | |
|---|---|
| B01J 27/055 | (2006.01) |
| B01J 27/16 | (2006.01) |
| B01J 27/18 | (2006.01) |
| C10L 1/26 | (2006.01) |
| C10L 1/02 | (2006.01) |
| B01J 27/053 | (2006.01) |
| B01J 35/10 | (2006.01) |

(52) U.S. Cl.
CPC ....... B01J 27/1802 (2013.01); B01J 27/1806 (2013.01); B01J 35/1014 (2013.01); B01J 35/1038 (2013.01); B01J 35/1061 (2013.01); C10L 1/026 (2013.01); C11C 3/003 (2013.01); C10L 2200/0476 (2013.01); C10L 2200/0484 (2013.01); C10L 2270/026 (2013.01)

(58) Field of Classification Search
CPC ...... B01J 27/055; B01J 27/16; B01J 27/1802; B01J 27/1806
See application file for complete search history.

(56) References Cited

U.S. PATENT DOCUMENTS

| | | | | |
|---|---|---|---|---|
| 2009/0326252 | A1* | 12/2009 | Srinivas | B01J 23/28 554/157 |
| 2012/0240452 | A1* | 9/2012 | Erdoes, Jr. | B01J 8/006 44/388 |
| 2012/0295167 | A1* | 11/2012 | Holzapfel | C01B 25/45 429/319 |
| 2015/0018572 | A1* | 1/2015 | Oh | C07C 67/03 554/162 |

* cited by examiner

USE OF HETEROGENEOUS ACID CATALYSTS BASED ON MIXED METAL SALTS TO PRODUCE BIODIESEL

RELATED APPLICATION

This application claims priority to MX/a/2016/004133, filed Mar. 31, 2016, which is hereby incorporated by reference.

FIELD OF THE INVENTION

The present invention relates to the use of heterogeneous acid catalysts primarily Lewis in nature to produce biodiesel by the transesterification of triglyceride esters, preferably by the transesterification of fresh or used vegetable oils, or oils and fats of animal origin, with alcohols in heterogeneous phase, in batch reactors or continuous flow systems, in ascending or descending mode, with yields exceeding 80%.

Such catalysts are preferably composed of mixed metal salts, such as lithium and aluminum phosphates and sulfates, in addition to their combinations with metallic cations, such as magnesium, titanium, zinc, zirconium and gallium, which provide adequate Lewis acidity; organic or inorganic porosity promoters, such as polysaccharides; and agglomerants, such as clays, kaolin and metal oxides of the type $M_xO_y$, where M=Al, Mg, Sr, Zr or Ti, among other metals of groups IA, IIA and IVB, x=1 or 2 and y=2 or 3, for the formation of particles with geometry and established size, such as extrudates, spheres, trilobe and raschig rings, among others.

The catalysts of the present invention may be used alone or in combination with other catalytic materials of a basic nature, such as magnesium oxides, aluminum oxides and sodium oxides to simultaneously promote esterification and transesterification reactions.

In this regard, it is important to note that the updated state of the art known to the applicant does not report any information on the catalytic activity of the catalysts such as the one of this invention to produce biodiesel.

BACKGROUND OF THE INVENTION

Biodiesel (biofuel) is a liquid obtained from natural lipids such as vegetable oils or animal fats, with or without prior use, through industrial processes of esterification and transesterification, and which is applied in the preparation of total or partial substitutes of the diesel or gasoil from petroleum. Biodiesel can be mixed with gas oil from the refining of petroleum in different quantities. Abbreviated notations are used according to the percentage by volume of biodiesel in the mixture: B100 in case of using only biodlesel, or other notations such as B5, B15, B30 or B50, where the numerals indicate the percentage by volume of biodiesel in the mixture.

Currently, the production of biodiesel is increasing and therefore the search for catalysts for its production has deserved a great development. The reaction to produce biodiesel consists of the transesterification of a molecule of triglyceride ester and three molecules of alcohol, which is typically methanol, to generate three molecules of fatty acid methyl ester FAME, which is biodiesel and a molecule of glycerine, accordingly to the following reaction scheme:

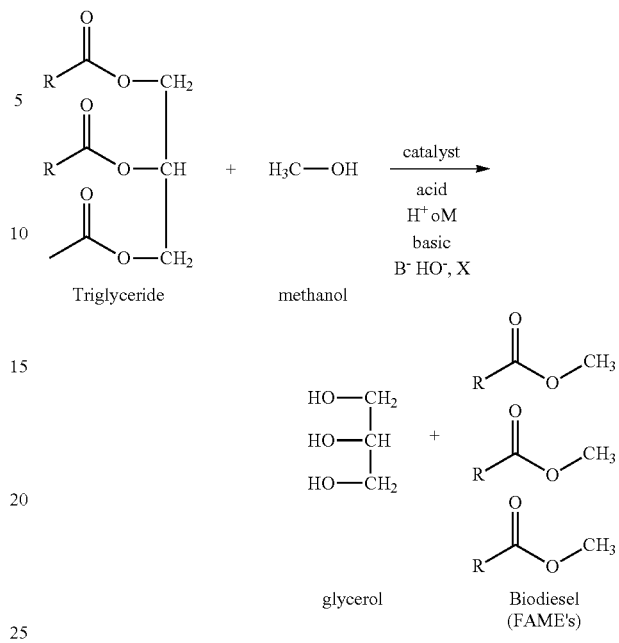

The process of transesterification of the triglyceride esters with methanol can be described in three steps: the triglyceride generates a fatty acid methyl ester molecule, FAME, and a diglyceride. The diglyceride in turn generates another molecule of FAME and a monoglyceride, which in turn generates the third molecule of FAME and glycerine. This sequence of reactions is carried out in the presence of basic catalysts which act on the alcohol to increase its attack reactivity or by acid catalysts acting on the oxygen of the ester in the triglyceride or the diglyceride or monoglyceride to activate the attack of the alcohol.

In the article Advances in Heterogeneous Catalysis for Biodiesel Synthesis, Top Catal. 53, 721-736, 2010, Yan et al., describe both the limitations of homogeneous or first generation catalysts, which act in the same reaction phase as the advantages of heterogeneous or second generation catalysts.

The limitations of the homogenous or first generation catalysts are:
a) their use is normally limited to batch processing, and are essentially highly corrosive acids or bases;
b) the stages of the homogeneous biodiesel production process are time consuming and highly expensive to process because the process comprises the steps of: oil pretreatment, catalytic transesterification, fatty acid methyl ester (FAME)/glycerin separation, neutralization of the residues of the homogeneous catalyst, distillation of methanol, washing with water of the FAME phase, and vacuum drying of the desired products;
c) it is impossible to reuse the homogeneous catalyst in reaction cycles as it is lost in the waste streams;
d) separation of the products requires a post-treatment with large volumes of water to neutralize the catalyst residues which generates waste water that must be treated before its release into the environment;
e) the homogeneous catalyst is sensitive to the free fatty acids (FFA) and water present in vegetable oils.

The advantages of heterogeneous or second generation catalysts are as follows:

a) The catalyst is not lost, it can be recovered from the reaction medium and subjected to several reaction cycles;
b) can be used in packed-bed reactors for continuous flow processes;
c) The post-treatment of product is not required or reduced, significantly reducing the ecological impact by avoiding the liquid wastes generated by the purification of the products; and
d) The microcrystalline structure of the catalyst surface is stable, which extends its useful life.

Acid type catalysts may be defined as oxygen carbonyl activators of the ester to increase its reactivity against the attack of the alcohol, typically methanol. These acid catalysts can be classified in those with Brönsted acid sites because they have interactions of carbonyl oxygen with catalytic proton ($H^+$) sites and those with Lewis acid sites because of interactions of carbonyl oxygen with cationic ($M^+$) sites in the catalyst In FIG. 1 the above is presented, emphasizing experimental evidence showing the type of acidity on the surface of the catalyst by an infrared spectrum which describes the adsorption of a Lewis base, such as pyridine, on an acid surface. The interaction of the acid sites on the surface with the pyridine molecule generates different bands, being the characteristics for Brönsted acid sites those that appear at 1,545 $cm^{-1}$ and the characteristics for Lewis acid sites appear at 1,445 $cm^{-1}$ and the intermediate of 1,490 $cm^{-1}$ for both interactions.

section (a) of FIG. 1 shows how the acid catalyst with Brönsted (H') sites acts on the triglyceride molecule activating it for the transesterification reaction;
in section (b) of FIG. 1 it is shown how the acid catalyst with Lewis (M') sites acts on the triglyceride molecule activating it for the transesterification reaction; and
section (c) of FIG. 1 shows a catalyst having both types of sites.

These interactions are also present in diglycerides and monoglycerides activating them for transesterification reactions with an alcohol, such as methanol. Thus, we can say that the catalysts of acidic nature to activate the triglyceride, diglyceride or monoglyceride molecules act at the promoter level of the C=O ester.

Catalysts with Brönsted acidity, such as heteropolyacids (HPAs), have shown high catalytic activity, yield and conversion, in combination with monovalent cations, such as $Cs^+$. The HPAs based on Nb and W supported on W—Nb, tungstated zirconia, tantalum pentoxide and silver have shown more resistance to catalyst leaching, as described in the following bibliographic citations.

Katada N. et al., in Applied Catalysis A General, (2009), 363 (164: 168); studied solid acid catalysts derived from HPAs with W and Nb. They found that under a calcination temperature of 773K, W and the HPAs based on Nb and supported on $WO_3$-Niobia ($WO_3$—$Nb_2O_5$) are transformed into NPNbW/W—Nb formulations Insoluble in the reaction mixture and with high catalytic activity for the transesterification of triolein and ethanol to ethyloleate. The reaction rate is increased when methanol is used instead of ethanol. Due to the potential and catalytic stability during at least 4 days of reaction of these catalysts, the authors recommend carrying out the reaction in fixed-bed and continuous flow.

Shi et al., in Chemical Engineering & Technology (2012), 35 (2), 347-352, describe that HPAs were used as triglyceride transesterification catalysts, arguing for both Brönsted and Lewis acidity properties. HPAs that are strong Brönsted acids, depending on their composition and the reaction medium, possess good thermal stability, high acidity and high oxidizing capacity and are water tolerant. Among HPAs, 12-tungstophosphoric acid ($H_3PW_{12}O_{40}$) is chosen because of its high activity, since it shows a Keggin structure which is composed of a coordinated tetrahedral heteroatom of oxygen ($PO_4$) surrounded by 12 additions of atoms sharing oxygen atoms coordinated octahedral ($WO_6$) according to Oliveira C. F. et al. (Esterification of oleic acid with ethanol by 12-tungstophosphoric acid supported on zirconia. Appl Catal A-Gen 372: 153-161 (2010)).

Heterogeneous catalysts of acidic nature such as those based on sulfated zirconia have been reported, emphasizing that the carbonyl oxygen activating acid sites are of the Brönsted nature according to Rattanaphra et al., "Simultaneous Conversion of Triglyceride/Free Fatty Acid Mixtures into Biodiesel Using Sulfated Zirconia", Top Catal. 53: 773-782, 2010.

On the other hand, the esterification of palmitic acid with HPA catalyst was also carried out by Caetano et al. (Esterification of free fatty acids with methanol using heteropolyacids immobilized on silica. Catal Commun 9:1996-1999 (2008)), using heterogeneous catalysts: Tungstophosphoric acid (PW), molybdophosphoric acid (PMo), and tungstosilicic acid (SiW) immobilized in silica by the sol-gel technique, of them the PW proved to be the best catalyst for which it was studied with different concentrations of load in silica, obtaining 100% conversion of the palmitic acid with a concentration of 0.042 g PW/g silica.

Zeolites, on the other hand, because of their uniform pore structure, have clear advantages of having a system with interconnected pores, so that the entire surface of the solid is available for promoting the transesterification reaction. The surface must be hydrophobic to promote the preferential adsorption of hydrophobic fats on the surface of the catalyst and to avoid deactivation of the catalytic sites by the strong adsorption of polar compounds such as glycerin or water. Z. Helwani, M. R. et al., (Applied Catalysis A: General 363 (2009) 1-10) Review: Solid heterogeneous catalysts for transesterification of triglycerides with methanol: A review).

Alternatively, in the patent document by Tian et al., CN 103801282, "Solid base catalyst, and preparation method and application thereof", the use of an aluminum-Zn spinel catalyst ($ZnAl_xO_{1+1.5x}$ where x=1.5-2.5) doped with La is described. The basic solid catalyst is used in the transesterification reaction of fatty acid esters with an alcohol to produce biodiesel; is of high and stable activity during its use, and the active components are not lost.

In the patent document CN 103,752,297 "Zirconium-oxide catalyst for producing biodiesel, as well as preparation method and application of zirconium-oxide catalyst. 2014" a zirconium oxide catalyst is claimed to produce biodiesel in a tubular reactor at a reaction temperature of 250-300° C., reaction pressure of 7 to 14 MPa and volume ratio of alcohol-oil of 0.5:1 to 7:1. The catalyst is characterized by containing zirconium oxide of 80-95 weight %, aluminum oxide of 2-18 weight %, 1 to 17% titanium dioxide, 5 to 25% sodium bicarbonate and 10 to 50% sodium chloride; and in the patent document CN 103,706,384 "Preparation method of bio-diesel catalyst. 2014", there is provided a method of preparing a catalyst for the production of biodiesel in a continuous flow process in which the composition is $PO_4^{3-}/ZrO_2$ doped with rare earth metals such as La, Ce, Pr, Nd, etc.

The Institut Français du Petrole has developed an industrial level technology called Esterfip-H™, which refers to a continuous process of transesterification where the reaction is promoted by a heterogeneous catalyst, which is a zinc aluminate ($ZnAl_2O_4$) spinel, which promotes the transesterification reaction, without loss of catalyst. The reaction is carried out at an operating temperature of 180-220° C. and pressure of 40-60 bar (40.79-61.18 kg/cm$^2$). The yields obtained are greater than 98%, with an excess of methanol. However, the raw material must have a free fatty acid content lower than 0.25% and a water content lower than 1,000 ppm. (Juan A. Melero et al., Critical Review, Heterogeneous acid catalysts for biodiesel production: current status and future challenges, Green Chem., 2009, 11, 1285-1308).

In U.S. Pat. No. 5,908,946, "Stem R. et al., Institut Français du Petrole, Process for the production of esters from vegetable oils or animal oils alcohols" (1999), for the production of esters of linear monocarboxylic acids with vegetable oils of 6 to 26 carbon atoms or oils of animal origin are reacted with monoalcohols having a low molecular weight, for example of 1 to 5 carbon atoms, In the presence of a catalyst selected among of zinc oxide, mixtures of zinc oxide and aluminum oxide, and the zinc aluminates corresponding to the formula: $ZnAl_2O_4$, $xZnO$, and $Al_2O_3$ (with x and y being 0-2 each) and with a spinel-type structure, allowing the direct production in one or more stages of an ester that can be used as fuel and pure glycerin. To process vegetable oil, severe operating conditions are considered: temperatures of 170-250° C., pressures lower than 100 bar (101.97 kg/cm$^2$), with excess stoichiometric alcohol, achieving conversions of 80-85%. In the case of acid oil feeds, operating conditions of 180-220° C. are used, with pressures lower than 1 bar (1.02 kg/cm$^2$).

Considering metal phosphates as metal catalysts for transesterification of biodiesel, Xie et al., in Bioresource Technology (2012), 119, 60-65, describe acid catalysts for transesterification of triglyceride esters based on 30 wt % $WO_3$ supported in $AlPO_4$, which were tested in batch reaction systems at 180° C. for 5 h and a methanol/oil ratio of 30:1 at a dose of 5 weight % catalyst.

Other catalysis systems for transesterification consist of calcium phosphates from pyrolysis of animal bone, which generates hydroxyapatite at 800° C., as described by Obadiah et al., in Bioresource Technology (2012), 116, 512-516.

Also, in the patent document CN 103,484,258 "Method for preparing biodiesel by using nano hydroxyapatite to catalyze triglyceride 2014", a method is described for preparing biodiesel in the presence of a nanohydroxyapatite catalyst in concentration of 0.5 to 3 weight % and operating from 800 to 300° C. for 2 to 10 h.

Yin et al. Describe in Fuel (2012), 93, 284-287 the catalytic activity of $K_3PO_4$ at conditions of 220° C., a methanol-oil ratio of 24:1 and 1% of the catalyst resulting in a conversion of 95.6%.

Sodium phosphate has also been used as a transesterification catalyst for triglyceride esters in biodiesel production according to De Fillipis et al., In Energy & Fuels (2005), 19 (6), 2225-2228.

SUMMARY OF THE INVENTION

Lithium and aluminum phosphates and sulfates have not been considered so far, in addition to their combinations with metallic cations such as magnesium, titanium, zinc, zirconium and gallium, as heterogeneous phase acidic catalysts with a primarily Lewis nature in the transesterification reaction of triglyceride esters in heterogeneous phase to produce alkyl esters for biodiesel, in both, batch reaction systems and continuous flow reaction systems, in ascending or descending mode, with yields in higher than 80%.

On the other hand, a primary reason for effecting the heterogeneous phase transesterification reaction and the production of alkyl esters to produce biodiesel is to avoid contaminating liquid effluents and to eliminate undesirable side reactions such as the hydrolysis of triglycerides, diglycerides and monoglycerides into free fatty acids; in addition, in case of using catalysts of a basic nature, the saponification could generate soaps.

It is therefore an object of the present invention to use heterogeneous acid catalysts primarily Lewis in nature to produce biodiesel by the transesterification of triglyceride esters, preferably by transesterification of fresh or used vegetable oils or oils and fats of animal origin, with alcohols in heterogeneous phase, in batch reactor or continuous flow systems, in ascending or descending mode, with yields higher than 80%.

Another object of the present invention is a method for producing biodiesel from vegetable oils or animal fat using heterogeneous acid catalysts primarily Lewis in nature to produce biodiesel which are preferably composed of mixed metal salts such as lithium and aluminum phosphates and sulfates, in addition to their combinations with metallic cations such as magnesium, titanium, zinc, zirconium and gallium, which provide adequate Lewis acidity; organic or inorganic porosity promoters, such as polysaccharides; and binders, such as clays, kaolin and metal oxides of the type $M_xO_y$, where M=Al, Mg, Sr, Zr or Ti, among other metals of groups IA, IIA and IVB, x=1 or 2 and y=2 or 3, for the formation of particles with geometry and established size, such as extrudates, spheres, trilobe and raschig rings, among others.

A further object of the present invention is a method of producing biodiesel using heterogeneous acidic catalysts primarily Lewis in nature to produce biodiesel in batch or continuous flow systems in ascending or descending mode at the following operating conditions: temperature from 150 to 300° C., Residence time from 20 minutes to 20 h, velocity space from 0.1 to 5 h$^{-1}$, pressure 25-100 kg/cm$^2$ (24.5-98.07 bar), methanol/oil molar ratio of 10 to 40 and catalyst concentration of 0.001 to 20 weight % based on tri-, di- or monoglyceride.

Another object of the present invention is the use of heterogeneous acid catalysts primarily Lewis in nature in a method of producing biodiesel by the preparation of alkyl esters of alkyl by transesterification of tri-, di- or monoglycerides, such as those derived or obtained from oils of vegetable or animal origin, in particular palm, jatropha, castor, soybean and sunflower oils, where the R groups of the alcohoxy groups R$^1$O, R$^2$O and R$^3$O of the glycerides are from C$_1$ to C$_{24}$ and a C$_1$-C$_4$ alcohol such as methanol, in an alcohol:oil ratio of 3:1 to 50:1.

A further object of the present invention is the application of combinations of bifunctional catalysts in the same reaction system, where a catalyst with acidic nature is used to process high acid number charges and an alkaline nature catalyst is used to carry a method for transesterification of the reduced acidity charge to produce biodiesel in batch reactor or continuous flow systems in ascending or descending mode, at the following operating conditions: temperature from 150 to 300° C., residence time from 20 minutes to 20 h, space velocity from 0.1 to 5 h$^{-1}$, pressure from 25 to 100 kg/cm$^2$ (24.5 to 98.07 bar), methanol/oil molar ratio from 10 to 40 and catalyst concentration from 0.001 to 20 weight % based on tri-, di-, or monoglyceride.

In one embodiment of the invention, the catalyst comprises lithium-aluminum phosphates and/or lithium-aluminum sulfates. The catalyst can also include an additional metal sulfate or phosphate of magnesium, titanium, zinc, zirconium, gallium and/or silicon.

The method for the transesterification of triglycerides reacts to the triglyceride with an alcohol, such as methanol or ethanol, in the presence of the lithium aluminum sulfates or phosphates to obtain the transesterified ester. The resulting ester is generally a methyl ester or ethyl ester.

The preceding and further objects of the present invention will be described more clearly and in detail in the following chapters.

BRIEF DESCRIPTION OF THE DRAWINGS OF THE INVENTION

DETAILED DESCRIPTION OF THE INVENTION

The present invention relates to the use of heterogeneous acid catalysts primarily Lewis in nature in a method for producing biodiesel by the transesterification of mono-, di- and/or triglyceride esters, preferably by the transesterification of fresh or wasted vegetable oils, or oils and fats of animal origin, with alcohols in heterogeneous phase, in batch or continuous flow systems, in ascending or descending mode, with yields higher than 80%, at the following operating conditions: temperature from 150 to 300° C., residence time from 20 minutes to 20 h, velocity space from 0.1 to 10 $h^{-1}$, pressure of 25-100 kg/$cm^2$ (24.5-98.07 bar), methanol/oil molar ratio of 10 to 40 and catalyst concentration of 0.001 to 20 weight % based on tri-, di- or monoglyceride.

More specifically, the use of heterogeneous acid catalysts primarily Lewis in nature in a method of producing biodiesel by the preparation of alkyl esters of alkyl by transesterification of tri-, di- or mono-glycerides, such as those derived from oils of vegetable or animal origin, in particular palm, jatropha, castor, soybean and sunflower oils, where the R groups of the alcohoxyls $R^1O$, $R^2O$ and $R^3O$ of the glycerides are from $C_1$ to $C_{24}$ and a $C_1$-$C_4$ alcohol such as methanol, in an alcohol:oil ratio of 3:1 to 50:1.

In this respect, it is important to note that the transesterification of triglyceride esters with alcohols in a heterogeneous phase is preferably carried out:

In stirred tank with residence times of 20 minutes to 20 h for batch reaction systems, and in a continuous flow reactor, in ascending or descending mode, at a space velocity of 0.1 to 10 $h^{-1}$, pressure of 25 to 100 kg/$cm^2$, temperature of 150 to 300° C. and a methanol/oil molar ratio from 10 to 40, for continuous flow reaction systems.

On the other hand, a primary reason to carry out the heterogeneous phase transesterification reaction to produce biodiesel is to avoid contaminating liquid effluents and to avoid undesirable parallel reactions such as the hydrolysis of triglycerides, diglycerides and monoglycerides into free fatty acids, in addition to that in the case of catalysts of a basic nature, the saponification could generate soaps.

Figure 1:
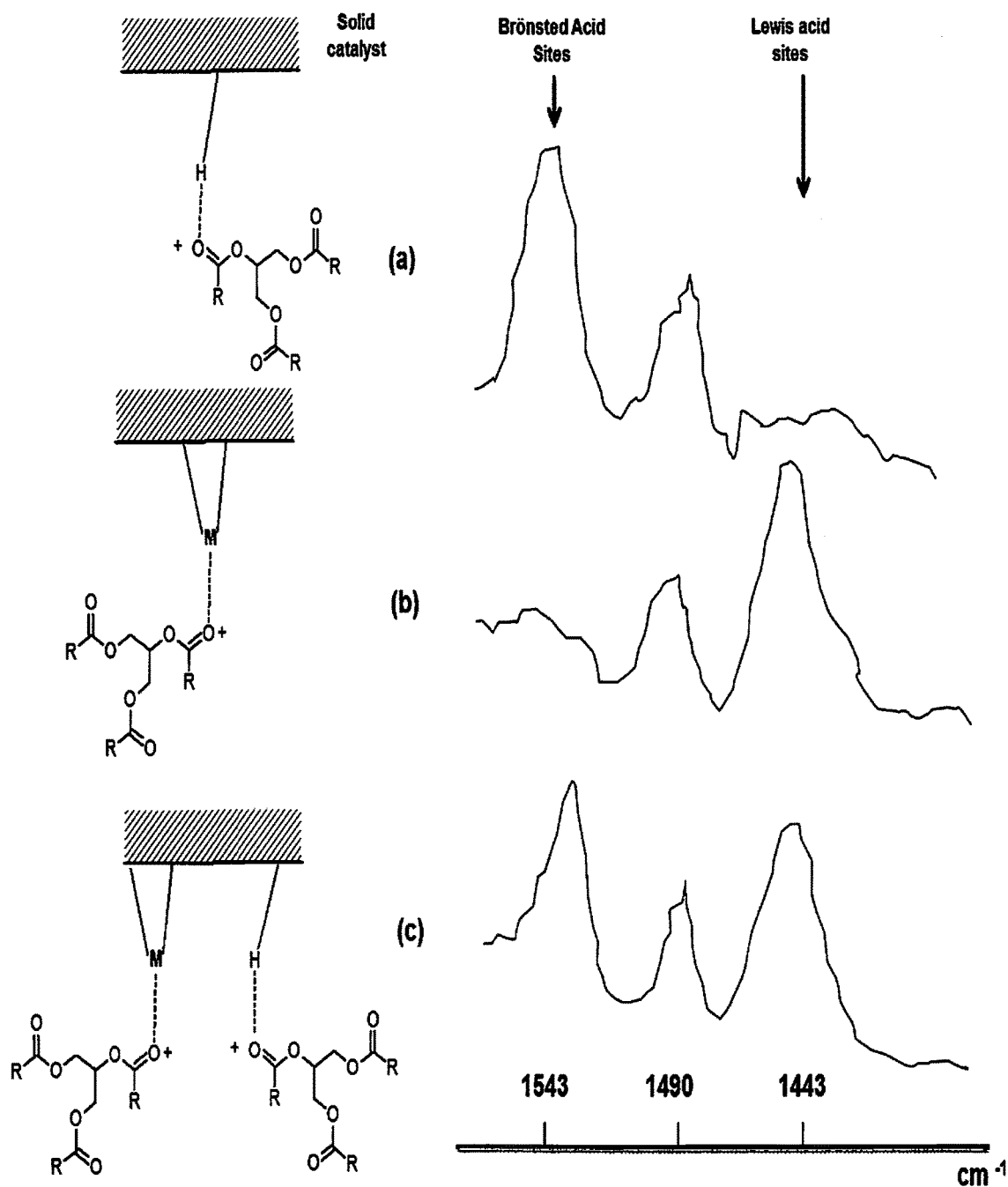
FIG. 1 shows the classification of acid catalysts according to Brönsted acid sites by having interactions of carbonyl oxygen with proton ($H^+$) sites on the catalyst and those with Lewis acid sites due to interactions of carbonyl oxygen with the cationic sites ($M^+$).
Figure 2:
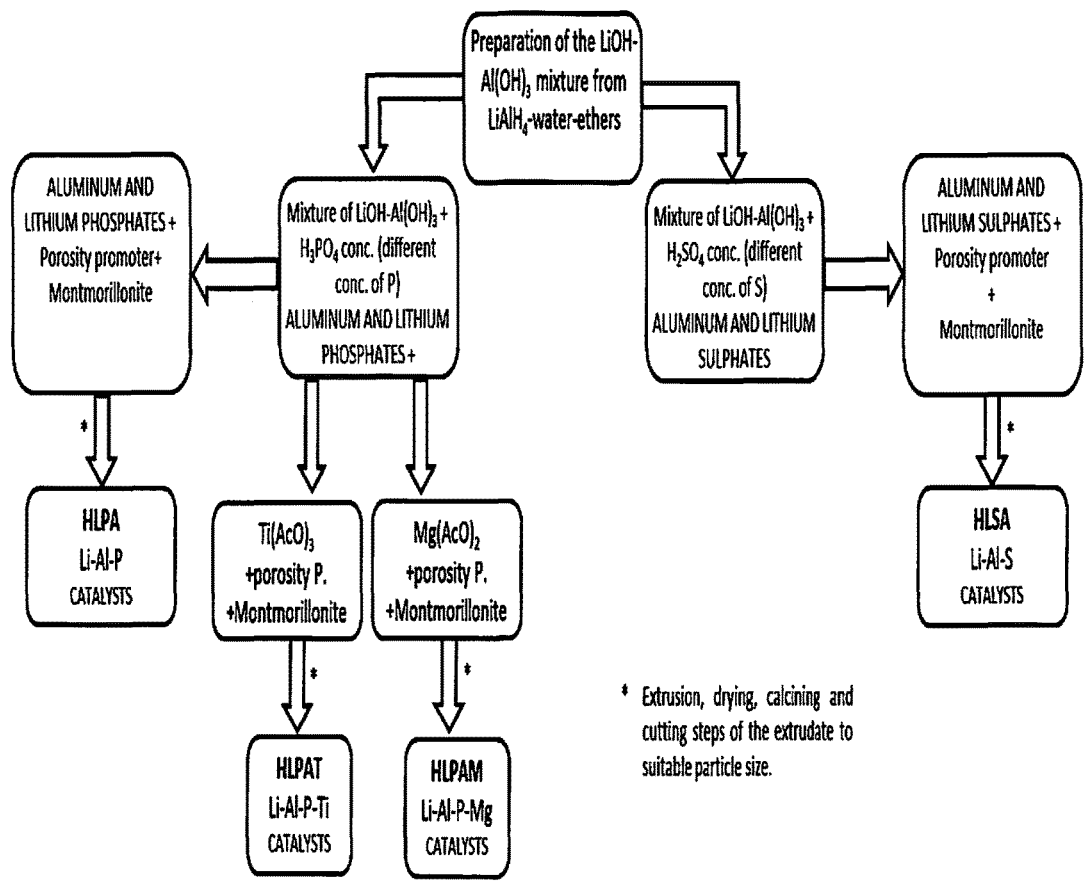
FIG. 2 is a flow chart for the preparation of heterogeneous acid catalysts based on mixed metal salts, preferred by the present invention to produce biodiesel, HLPA, HLPAT and HLPAM series, respectively; and also applicable to HLSAT and HLSAM series with any precursor source of S and Ti.

FIG. 2 shows in general a scheme for the preparation of heterogeneous acid catalysts based on mixed metal salts, preferred by the present invention to produce biodiesel, HLPA, HLPAT and HLPAM series, respectively; and additionally, applicable to HLSAT and HLSAM series with any precursor source of S and Ti.

Figure 3:
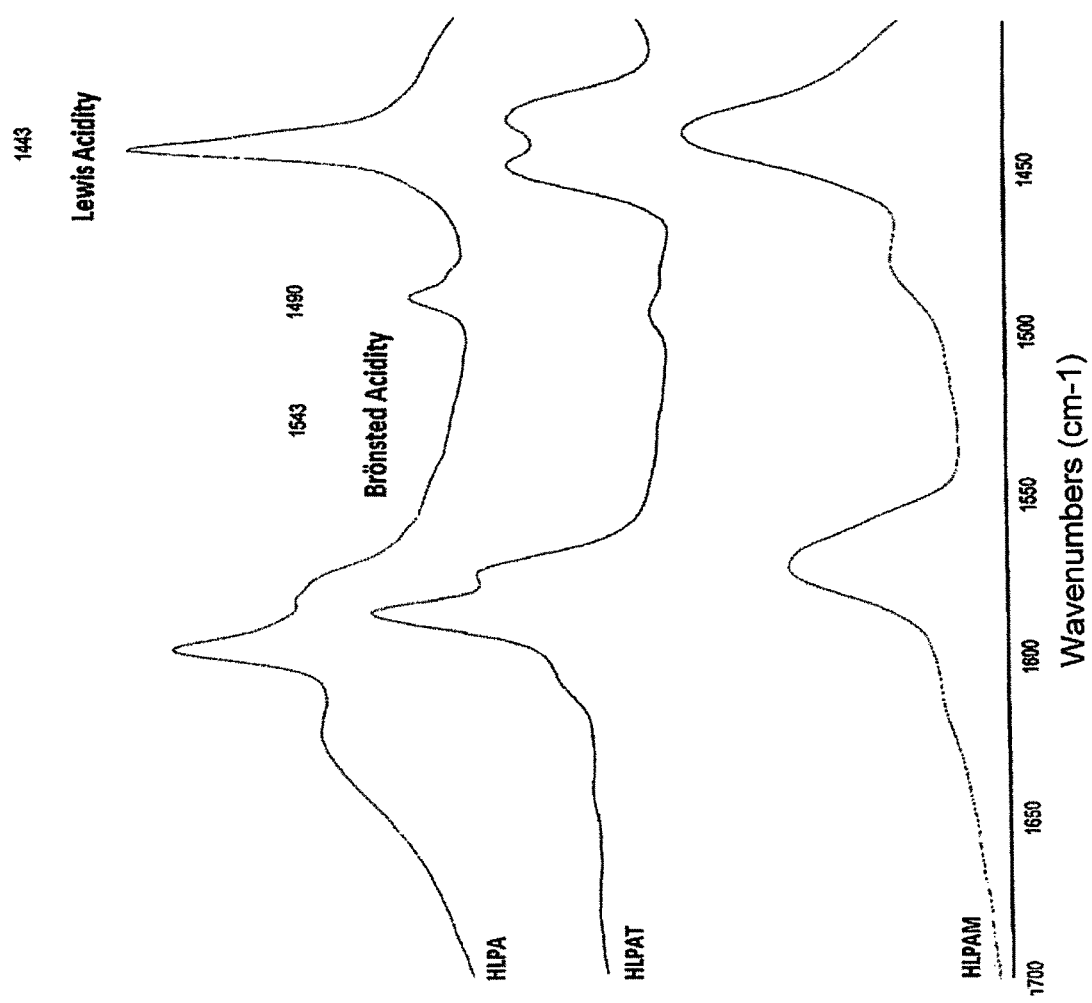
FIG. 3 is a graph showing the Lewis acidity sites of the heterogeneous acid catalysts based on mixed metal salts, preferred by the present invention to produce biodiesel, HLPA, HLPAT and HLPAM series, determined by Fourier Transform Infrared Spectrometry (FTIR).
Figure 4:
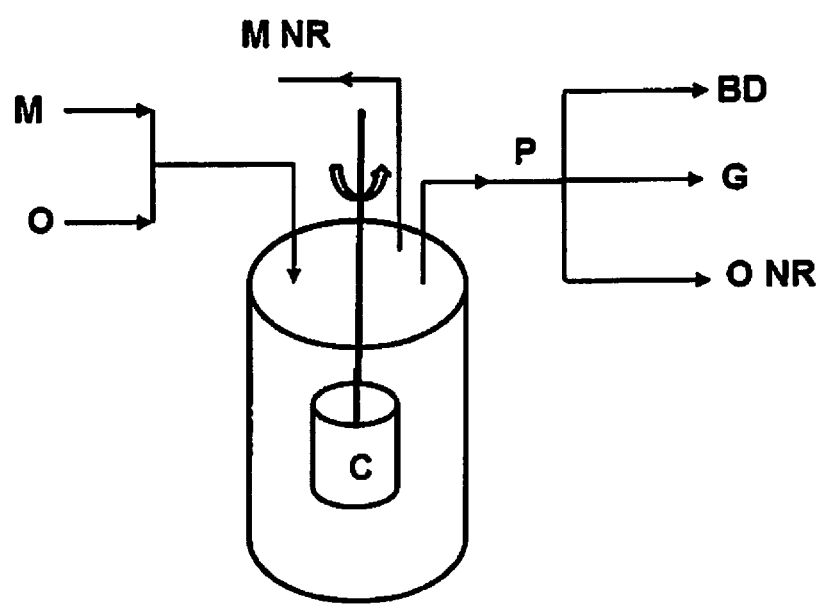
FIG. 4 is a batch reactor scheme for evaluating heterogeneous acid catalysts primarily Lewis in nature to produce biodlesel by transesterification of triglyceride esters with alcohols in a heterogeneous phase.

In this regard, FIG. 3 shows a graph of the Lewis acidity sites of heterogeneous acid catalysts based on mixed metal salts, preferred by the present invention to produce biodiesel, HLPA, HLPAT and HLPAM series, respectively, determined by Fourier Transform Infrared Spectrometry (FTIR).

Lithium and aluminum phosphates and sulfates have not been considered so far, in addition to their combinations with metallic cations such as magnesium, titanium, zinc, zirconium and gallium, as heterogeneous phase acid catalysts with a primarily Lewis nature in the transesterification reaction of triglyceride esters in heterogeneous phase to produce biodiesel, in both batch reaction systems and in continuous flow reaction systems, In ascending or descending mode, with yields higher than 80%. In one embodiment, the lithium and aluminum phosphates and/or sulfates catalyst further includes a basic catalytic material, such as magnesium oxide, aluminum oxide and sodium oxide to promote the esterification and transesterification reaction.

The heterogeneous acid catalysts primarily Lewis nature employed by the present invention for producing biodiesel are preferably composed of mixed metal salts, such as lithium and aluminum phosphates and sulfates, with the following percentages of metals by weight of the catalyst: lithium of up to 5 weight % and generally 0 to 5 weight %, preferably 0.1 to 3 weight %, and aluminum up to 15 weight % and generally from 0 to 15 weight %, preferably 0.3 to 10 weight %; in addition to combinations of the lithium and aluminum phosphates and/or sulfates with metal cations in concentrations of 0 to 40 weight % of the catalyst, such as magnesium, titanium, zinc, zirconium, gallium and silicon, preferably titanium, magnesium and silicon, in concentrations of 0.2 to 30 weight %, which provide adequate Lewis acidity; organic or inorganic porosity promoters in concentrations of from 0.05 to 25% by weight of the wet base catalyst, preferably up to 12 weight % and generally from 0 to 12 weight %, such as polysaccharides; and binders in concentrations of 1 to 20 weight % of the catalyst, such as clays, kaolin and metal oxides of the type MxOy, where M=Al, Mg, Sr, Zr or TI, among other metals of groups IA, IIA and IVB, X=1 or 2 and y=2 or 3, preferably clays in concentrations of 3 to 15 weight %, for the formation of particles with geometry and size, such as extrudates, spheres, trilobes and raschig rings, among others; having the following properties: surface area of 10 to 180 $m^2$/g, preferably 30 to 80 $m^2$/g, pore volume of 0.1 to 0.5 $cm^3$/g, preferably 0.1 to 0.3 $cm^3$/g, and average pore diameter 100 to 200 Å, preferably 110 to 170 Å. The lithium and aluminum phosphate and sulfate catalyst can be prepared by the method disclosed in commonly owned MX/a/2016/004132 and its corresponding US patent application filed concurrently herewith, which is hereby incorporated by reference in its entirety.

The mixed metal salts in addition to their combinations with metallic cations are preferably:
  Lithium and aluminum phosphates and sulfates (HLPA and HLSA Series, respectively),
  Lithium, aluminum and titanium phosphates and sulfates (HLPAT and HLSAT series respectively), and
  Phosphates and sulfates of lithium, aluminum and magnesium (HLPAM and HLSAM Series respectively).
the polysaccharide used as a porosity promoter is preferably amylose-amylopectin (starch).
the clays used as binders are preferably of the montmorillonite type.

The evaluation of the heterogeneous acid catalysts primarily Lewis acids to produce biodiesel by the transesterification of fresh or wasted vegetable oils or oils and fats of animal origin was carried out in a batch bank reactor with a capacity of 300 ml of the Parr brand, as well as in a packed bed reactor and continuous flow. The experiments allowed to select the operating conditions to evaluate the catalytic materials in development Temperature=200° C., P=40 kg/cm$^2$, MeOH/Oil mole ratio=18 and residence time of 6-24 h, and for the packed reactor at temperatures of 150-300° C., P=25-100 kg/cm$^2$, mol ratio MeOH/Oil=10-40 and space velocity from 0.1 to 5 h$^{-1}$.

Similarly, combinations of the acid catalyst with a basic catalyst based on metal oxides were evaluated to carry out the transesterification of the feed, primarily, by reducing its free fatty acid content with the acid catalyst and subsequently with the catalyst alkaline nature, produce biodiesel in batch reaction systems or continuous flow in ascending or descending mode.

EXAMPLES

Some practical examples of the present invention will now be described, for a better understanding thereof, without limiting its scope.

The evaluation of heterogeneous acid catalysts primarily Lewis acids to produce biodiesel by transesterification of triglyceride esters with alcohols in a heterogeneous phase was carried out using a refined, bleached and deodorized (RBD) palm oil with the properties presented in Table 1, which was subjected to transesterification in both batch reactor (Examples 1 and 2), and in continuous flow reactor (Examples 3 to 12), with a light or lower alcohol having the properties shown in Table 2; obtaining a transesterified product containing fatty acid methyl esters (FAME).

TABLE 1

Properties of RBD palm oil, used as a feed in the Examples of the present invention.

| Properties | Units | Values |
|---|---|---|
| Density @ 50° C. | | 0.888-0.889 |
| Kinematic viscosity @ 40° C. | cSt (mm$^2$/s) | 1.9-6.0 |
| Acid number | mgKOH/g | 0.5-0.8 |
| Iodine Index | | 46-56 |
| Fatty acid | % peso | |
| C-12:0 Lauric | | 0.1-1.0 |
| C-14:0 Myristic | | 0.9-1.5 |
| C-16:0 Palmitic | | 41.8-46.8 |
| C-16:1 Pelmitoleic | | 0.1-0.3 |
| C-18:0 Stearic | | 4.5-5.1 |
| C-18:1 Oleic | | 37.3-40.8 |
| C-18:2 Linoleic | | 9.1-11.0 |
| C-18:3 Linolenic | | 0.4-0.6 |
| C-20:0 Arachidic | | 0.2-0.7 |
| Diglyceride | % peso | 3.0-7.6 |

TABLE 2

Properties of methanol used as feed, in the Examples of the present invention.

| Specification | Unit | Values |
|---|---|---|
| Distillation at 780 mmHg | ° C. | 1.0% max. Includes 64.6 |
| Purity | Wt % | 99.85-99.99 |
| Color | Pt—Co | 5 máx. |
| Acidity (acetic acid) | Wt % | 0.003 máx. |
| Permanganate test | Minutes | 50 min |
| Acetone | Wt % | 0.003 máx. |
| Water | Wt % | 0.10 máx. |
| Non-volatile matter | Wt % | 0.001 máx. |
| Carbonisable Substances | Pt—Co | 50 máx. |
| Specific Gravity 20/20° C. | — | 0.7920-0.7932 |

Example 1

Evaluation in Batch Reactor with Refined, Bleached and Deodorized Palm Oil (RBD)

These tests were performed in a system as shown in FIG. No. 4, where:
  M=methanol,
  O=oil,
  C=catalyst,
  M NR=unreacted methanol,
  P=products,
  BD=biodiesel,
  G=glycerol, and
  O NR=unreacted oil.

1. Six 5 mL vials, each with ⅙ of the total weight of the catalyst to be evaluated (5% oil base) were prepared as described in Table No. 3, with particle size equivalent to mesh numbers 30 and 40; and six 50 mL wide mouth flasks, each with ⅙ of the total diluent (SIC) weight and 30-40 mesh particle size. The weight of the empty basket of the catalyst and of the empty vessel of the Parr reactor were recorded.
2. The contents of a 5 mL glass vial were mixed with the catalyst contained in one of the 50 mL wide-mouth flask containing the diluent (SiC), this was repeated for the remaining 5 vials and 5 flask, and each flask was mixed to obtain an homogeneous solid mixture.
3. Each section of the catalyst basket was charged with 2 of the flask of the diluent and catalyst mixture, taking care of the preservation of the catalyst-diluent mixture. The weight of the basket loaded with the catalyst and diluent mixture was recorded.
4. The catalyst basket was introduced into the reactor. The oil and methanol feeds were weighed, then poured into the Parr reactor vessel. The reactor was immediately sealed and fed with $N_2$ to an initial pressure of 7 kg/cm$^2$; upon reaching this pressure the $N_2$ feed was suspended. The cooling water pass valve was opened ⅛ turn.

5. The Parr reactor software was programmed to take the heating to 200° C. and the reactor controller was set at a stirring speed of about 750 rpm. The heating level II (high power) was maintained until reaching 100° C. and then switched to the heating level I (low power). The heating log was updated every 5 min. According to the heating of 100 to 200° C. continuously, the cooling water pressure of the stirrer was monitored to maintain constant flow and prevent the temperature from falling due to a high water flow or the agitator section being heated due to a decrease in water flow.
6. The start of the reaction was considered when the reactor reached 200° C. and 40 kg/cm$^2$ and recording of the pressure, temperature, stirring rate and heating percentage was performed every 15 min for 6 hours.
7. After 6 h of reaction at 200° C. and 40 kg/cm$^2$, heating was stopped in the reactor controller and the gradual cooling of the reactor was started until the initial temperature and a pressure of 7 kg/cm$^2$ were reached.
8. The reactor was opened and the obtained oily product was deposited in a 253-mL pre-tared wide-mouth clear Flask. The weight of the flask was recorded with the oily product. The weight of the reactor containing the basket was recorded with the wet catalyst. The reactor was closed with the wet basket and $N_2$ was fed to a pressure of 7 kg/cm$^2$, the reactor was left standing for the next experiment.
9. The oily product was centrifuged using an IEC CU-5000 centrifuge at 1,500 rpm for 10 min, according to the procedure established for the transesterification products. The obtained phases were separated in the centrifugation and the weight and volume of these were registered to realize the mass balance. The phase separation was performed with Pasteur pipettes, initiating the pipetting of the sample from the lower phase. In addition, the color and appearance of the phases were recorded and a sample of the phase was taken.
10. The biodiesel phase was then subjected to simple distillation to remove excess methanol, starting at 65° C. and ending at 100-120° C. A biodiesel sample was taken for analysis by gas chromatography and mass spectrometry (GC-MS) and to analyze the composition of FAME and total content of these.
11. At the end of the experiment, the diluent and catalyst were discharged from the basket. In a Soxhlet kit with chloroform at 50° C. and constant atmospheric pressure, the catalyst and the diluent were cleaned. After cleaning the catalyst and the diluent were deposited in a 120 mL amber flask with wide mouth and thread.

The catalysts prepared and evaluated in the batch reactor showed FAME yield values determined by Nuclear Magnetic Resonance (NMR) from 82 to 90.7 weight %.

Table 3 shows the evaluated catalysts and their behavior in terms of biodiesel yield and FAME content, emphasizing the effect of the Metal/P (M/P) ratio for mixed metal salts and their combinations with Metal cations prepared with lithium, aluminum, titanium and magnesium according to the used series, and starch added as a porosity promoter. Likewise, the surface area determined by the BET method is shown

TABLE 3

Behavior of heterogeneous acid catalysts in a batch reactor with RBD palm oil based on their Metal/P ratio[1], starch content and surface area.

| Catalyst | Li/P | Al/P | M/P | Starch (g) | Surface area (m$^2$/g) | % Yield[2] (RMN) | % Content of FAME |
|---|---|---|---|---|---|---|---|
| HLPA-6 | 1.17 | 4.57 | | 10.9 | 170.40 | 88.67 | 89.7 |
| HLPA-16 | 1.20 | 4.65 | | 3.7 | 137.05 | 89.67 | 91.3 |
| HLPA-20 | 0.08 | 0.32 | | 4.7 | 20.87 | 82.00 | 89.3 |
| HLPAT-1 | 0.02 | 0.06 | Ti/P 0.05 | 0.0 | 94.77 | 85.33 | 91.8 |
| HLPAM-3 | 1.19 | 4.63 | Mg/P 2.08 | 4.7 | 52.08 | 90.70 | 93.4 |

[1]Wet base;
[2]Yield

Example 2

The palm oil RBD, having the properties presented in Table 1, was subjected to the step of transesterification with methanol, with the properties shown in Table 2, using the heterogeneous catalyst HLSA-4 whose composition is Al—Li—S at concentrations of 1 wt % Li, 3.9 wt % Al and 10.8 wt % S on a dry basis. The transesterification reaction was carried out in a batch reactor with 5% base catalyst to the oil, under the operating conditions shown in Table 4.

TABLE 4

Operating conditions of the catalytic transesterification step of the RBD palm oil of Example 2.

| Variable | Condition |
|---|---|
| Pressure, kg/cm$^2$ | 40 |
| Temperature, ° C. | 200 |
| Reaction time, h | 6 |
| Mole ratio MeOH/Oil | 18 |

The transesterified product was obtained with a biodiesel yield of 71.7 wt % with a FAME content of 65.1 wt %

Example 3

An evaluation with a heterogeneous acid catalyst of primarily Lewis nature, in composition Al—P—Zr, with concentrations of 20 weight % of $P_2O_5$, 24 weight % of $ZrO_2$, and 56 weight % of $Al_2O_3$, was carried out in equal parts, with a catalyst having an alkaline nature, containing Mg:Al in a weight ratio of 1.1:1, to produce biodiesel by transesterification of triglyceride esters with alcohols in a heterogeneous phase, using as feed an animal fat with basic density properties of 0.9160 g/mL measured at 20° C., kinematic viscosity at 37.8° C. of 42.3 cSt (mm$^2$/s), acid value of 5.04 mg KOH/g, moisture of 0.5 weight % and Impurities content of 0.5 weight %.

The animal fat was subjected to the step of transesterification with methanol, with the properties shown in Table 2, using the heterogeneous acid catalyst in combination with the alkaline catalyst. The transesterification reaction was carried out in a batch reactor at the operating conditions shown in Table 5 to give a transesterified product containing methyl esters of fatty acids (FAME).

TABLE 5

Operating conditions of the catalytic transesterification step of animal fat, from Example 3.

| Variable | Condition |
|---|---|
| Pressure, kg/cm$^2$ | 40 |
| Temperature, ° C. | 200 |
| Reaction time, h | 3 |
| Mole ratio MeOH/Oil | 18 |

The transesterified product was obtained with a biodiesel yield of 85.7 wt % with a FAME content of 73.6 wt %

Evaluation in Continuous Flow Reactor

Figure 5:
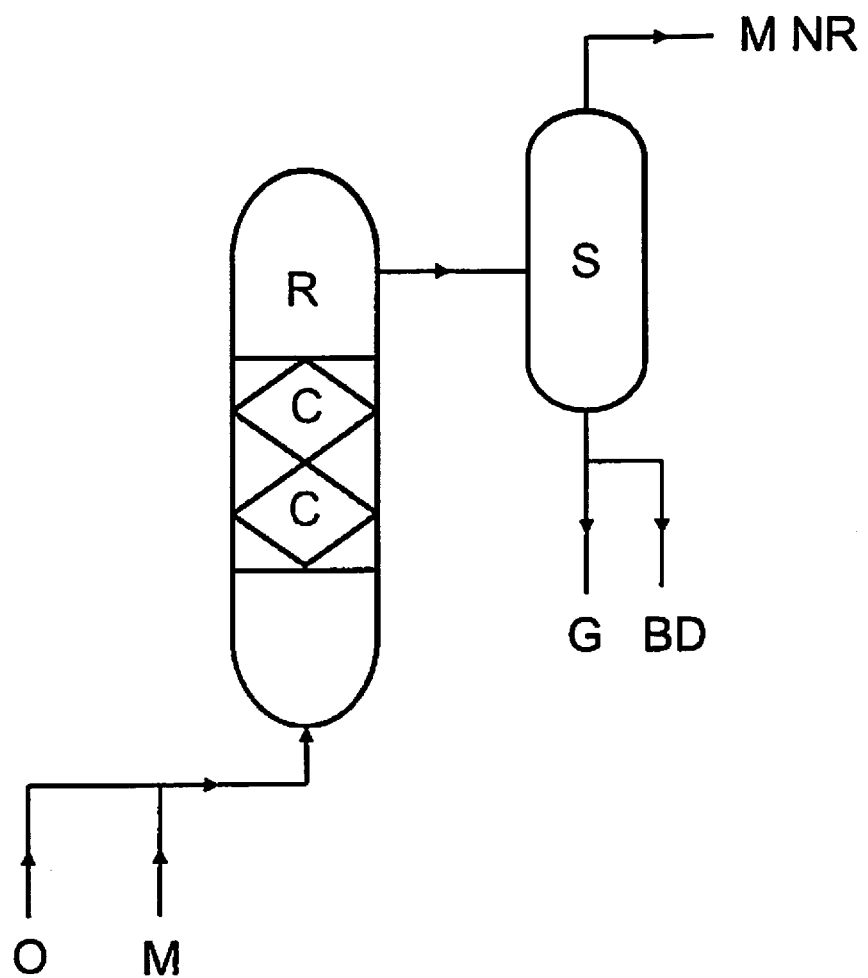
FIG. 5 shows a continuous flow reactor scheme for evaluating heterogeneous acid catalysts primarily Lewis in nature to produce biodiesel by transesterification of triglyceride esters with alcohols in a heterogeneous phase.

The evaluation of heterogeneous acidic catalysts primarily Lewis to produce biodiesel by transesterification of triglyceride esters with alcohols in a heterogeneous phase in an upstream or downstream continuous flow reactor was carried out under the following conditions: LHSV=0.5 h$^{-1}$, mole ratio methanol/oil (RM)=18, in an upflow microreaction plant, according to FIG. 5 where:

O=oil,
M=methanol,
C=catalyst,
R=tubular reactor,
S=separator,
M NR=unreacted methanol,
G=glycerol,
BD=biodiesel, and
O NR=unreacted oil Tables 6 and 7 describe the properties of the catalysts evaluated in the continuous flow reactor, which were HLPA-16, whose composition is Al—Li—P, and HLPAM-3, whose composition is Al—Li—P—Mg, respectively.

TABLE 6

Catalyst Properties HLPA-16, used in the Examples of the present invention.

| Properties Composition[1], weight % | Value |
|---|---|
| Lithium | 1.95 |
| Aluminum | 7.59 |
| Phosphorus | 1.63 |
| Particle size, mm | 0.42-0.59 |

[1]dry basis

TABLE 7

Catalyst Properties HLPAM-3, used in the Examples of the present invention.

| Properties Composition[1], weight % | Valor |
|---|---|
| Lithium | 0.90 |
| Aluminum | 3.5 |
| Phosphorus | 0.43 |
| Magnesium | 1.6 |
| Particle size, mm | 0.42-0.59 |

[1]dry basis

Example 4

The evaluation of the HLPA-16 catalyst, the properties of which were described in Table 6, was carried out in the transesterification reaction of the RBD palm oil, with the properties presented in Table 1, and methanol, with the properties shown in Table 2. The test consisted of reaching the initial reaction conditions at LHSV=0.5 h$^{-1}$, RM=18, 40 kg/cm$^2$ pressure and 200° C. temperature and maintaining these conditions in ascending flow for a 24 hours term to attain the stability of the catalyst and the operation. Subsequently, 5 material balances of 12 hours each were made under these conditions, sampling the reactor products. The evaluation of this catalyst was continued with the temperature rise from 200 to 215° C. and the pressure was increased from 40 to 50 kg/cm$^2$ to ensure that the reaction was carried out in liquid phase, keeping the other conditions constant, once reached the temperature, it was maintained at that point for 12 hours and 3 balances of 12 hours each were made. A transesterification product containing fatty acid methyl esters (FAME) was obtained in excess of 90%.

Example 5

The RBD palm oil, having the properties presented in Table 1, was subjected to the step of transesterification with methanol, with the properties shown in Table 2, using the heterogeneous catalyst HLPAM-3 whose composition is Al—Li—P—Mg with the properties described in Table 7. The transesterification reaction was carried out in a fixed-bed reactor with flow upstream to the operating conditions shown in Table. 8.

TABLE 8

Operating conditions of the catalytic transesterification step of the RBD palm oil of Example 5.

| Variable | Condition |
|---|---|
| Pressure, kg/cm$^2$ | 40 |
| Temperature, ° C. | 200 |
| Liquid hourly space velocity (LHSV), h$^{-1}$ | 0.5 |
| Mole ratio MeOH/Oil | 18 |

The transesterified product was obtained with a biodiesel yield of 89.3 wt % with a FAME content of 89.6 wt %.

Example 6

According to Example 5, the catalytic transesterification step of the RBD palm oil using the heterogeneous catalyst HLPAM-3 of Table 7 was carried out under the operating conditions shown in Table 9.

TABLE 9

Operating conditions of the catalytic transesterification step of RBD palm oil of Example 6.

| Variable | Condition |
|---|---|
| Pressure, kg/cm$^2$ | 40 |
| Temperature, ° C. | 215 |
| Liquid hourly space velocity (LHSV), h$^{-1}$ | 0.5 |
| Mole ratio MeOH/Oil | 18 |

The transesterified product was obtained with a biodiesel yield of 91.3 wt % with a FAME content of 91.4 wt %.

Example 7

According to Example 5, the catalytic transesterification step of the RBD palm oil using the prototype heterogeneous catalyst HLPAM-3 of Table 7 was carried out under the operating conditions shown in Table 10.

TABLE 10

Operating conditions of the catalytic transesterification step of the RBD palm oil of Example 7.

| Variable | Condition |
| --- | --- |
| Pressure, kg/cm² | 55 |
| Temperature, ° C. | 220 |
| Liquid hourly space velocity (LHSV), h⁻¹ | 0.3 |
| Mole ratio MeOH/Oil | 18 |

The transesterified product was obtained with a biodiesel yield of 82.9 wt % with a FAME content of 93.7 wt %.

Example 8

According to Example 5, the catalytic transesterification step of the RBD palm oil using the prototype heterogeneous catalyst HLPAM-3 of Table 7 was carried out under the operating conditions shown in Table 11.

TABLE 11

Operating conditions of the catalytic transesterification step of the RBD palm oil of Example 8.

| Variable | Condition |
| --- | --- |
| Pressure, kg/cm² | 55 |
| Temperature, ° C. | 220 |
| Liquid hourly space velocity (LHSV), h⁻¹ | 0.3 |
| Mole ratio MeOH/Oil | 36 |

The transesterified product was obtained with a biodlesel yield of 86.7 wt % with a FAME content of 96.0 wt %.

Example 9

According to Example 5, the catalytic transesterification step of the RBD palm oil using the prototype heterogeneous catalyst HLPAM-3 of Table 7 was carried out under the operating conditions shown in Table 12.

TABLE 12

Operating conditions of the catalytic transesterification step of the RBD palm oil of Example 9.

| Variable | Condition |
| --- | --- |
| Pressure, kg/cm² | 70 |
| Temperature, ° C. | 230 |
| Liquid hourly space velocity (LHSV), h⁻¹ | 0.3 |
| Mole ratio MeOH/Oil | 18 |

The transesterified product was obtained with a biodiesel yield of 88.3 wt % with a FAME content of 91.9 wt %.

Example 10

According to Example 3, the step of catalytic transesterification of animal fat was carried out using a heterogeneous acidic catalyst with primarily Lewis nature in combination with a catalyst having an alkaline nature to produce biodlesel. The transesterification reaction was carried out in an upflow fixed bed reactor under the operating conditions shown in Table 13 to yield a transesterified product containing methyl esters of fatty acids (FAME).

TABLE 13

Operating conditions of the catalytic transesterification step of the RBD palm oil of Example 10.

| Variable | Condition |
| --- | --- |
| Pressure, kg/cm² | 40 |
| Temperature, ° C. | 200 |
| Liquid hourly space velocity (LHSV), h⁻¹ | 0.5 |
| Mole ratio MeOH/Oil | 18 |

The transesterified product was obtained with a biodlesel yield of 87.9 wt % with a FAME content of 75.5 wt %.

Example 11

According to Example 3, the step of catalytic transesterification of animal fat was carried out using a heterogeneous acidic catalyst with primarily Lewis nature in combination with a catalyst having an alkaline nature to produce biodiesel. The transesterification reaction was carried out in an upflow fixed bed reactor under the operating conditions shown in Table 14 to give a transesterified product containing fatty acid methyl esters (FAME).

TABLE 14

Operating conditions of the catalytic transesterification step of palm oil RBD of Example 11.

| Variable | Condition |
| --- | --- |
| Pressure, kg/cm² | 50 |
| Temperature, ° C. | 215 |
| Liquid hourly space velocity (LHSV), h⁻¹ | 0.5 |
| Mole ratio MeOH/Oil | 18 |

The transesterified product was obtained with a biodiesel yield of 87.6 wt % with a FAME content of 78.1 wt %.

Example 12

According to Example 3, the step of catalytic transesterification of animal fat was carried out using a heterogeneous acidic catalyst with primarily Lewis nature in combination with a catalyst having an alkaline nature to produce biodiesel. The transesterification reaction was carried out in an upflow fixed bed reactor under the operating conditions shown in Table 15 to give a transesterified product containing methyl esters of fatty acids (FAME).

TABLE 15

Operating conditions of the catalytic wtransesterification step of RBD palm oil of Example 12.

| Variable | Condition |
| --- | --- |
| Pressure, kg/cm² | 40 |
| Temperature, ° C. | 200 |
| Liquid hourly space velocity (LHSV), h⁻¹ | 1.0 |
| Mole ratio MeOH/Oil | 18 |

The transesterified product was obtained with a biodiesel yield of 77.1 wt % with a FAME content of 67.2 wt %.

Example 13

According to Example 3, the step of catalytic transesterification of animal fat was carried out using a heterogeneous acidic catalyst with primarily Lewis nature in combination with a catalyst having an alkaline nature to produce biodiesel. The transesterification reaction was carried out in a fixed bed reactor upflow under the operating conditions shown in Table 16 to give a transesterified product containing fatty acid methyl esters (FAME).

TABLE 16

Operating conditions of the catalytic transesterification step of the RBD palm oil of Example 13.

| Variable | Condition |
| --- | --- |
| Pressure, kg/cm$^2$ | 50 |
| Temperature, ° C. | 215 |
| Liquid hourly space velocity (LHSV), h$^{-1}$ | 1.0 |
| Mole ratio MeOH/Oil | 18 |

The transesterified product was obtained with a biodlesel yield of 87.1 wt % with a FAME content of 76.4 wt %.

What is claimed is:

1. A method of producing biodiesel by the transesterification of triglyceride esters with alcohols in the presence of a heterogeneous acid catalyst primarily Lewis acid in nature in heterogeneous phase, wherein said heterogeneous acid catalyst comprises mixed metal salts of lithium and aluminium phosphates and/or sulfates in a reactor, said method comprising feeding the triglyceride esters and alcohol to the reactor in batch or continuous flow, in descending or ascending mode, to obtain yields exceeding 80%, at the following operating conditions: temperature from 150 to 300° C., residence time from 20 minutes to 20 h, space velocity from 0.1 to 10 h$^{-1}$, pressure 25-100 kg/cm$^2$ (24.5-98.07 bar), alcohol/oil molar ratio of 10 to 40 and catalyst concentration of 0.001 to 20 weight % based on tri-, di- or monoglyceride.

2. The method of producing biodiesel according to claim 1, wherein the heterogeneous acid catalysts of mixed metal salts of lithium and aluminum phosphates and/or sulfates further comprise lithium in an amount of up to 5 weight %, and aluminum up to 15%, in addition to combinations with metal cations in concentrations of up to 40 weight % of the catalyst, where the metal cations are selected from the group consisting of magnesium, titanium, zinc, zirconium, gallium and silicon, to provide Lewis acidity; organic or inorganic porosity promoters in concentrations of from 0.05 to 25 weight % of a wet base catalyst, and binders in concentrations of 1 to 20 weight % of the catalyst, selected from the group consisting of clays, kaolin and metal oxides of the formula MxOy, where M=Al, Mg, Sr, Zr or Ti, X=1 or 2 and y=2 or 3, as particles selected from the group consisting of extrudates, spheres, trilobules and raschig rings.

3. The method of producing biodiesel according to claim 2, wherein the mixed metal salts of the catalyst, in addition to combinations with metal cations, are selected from the group consisting of:
   a. Phosphates and sulfates of lithium and aluminum,
   b. Lithium, aluminum and titanium phosphates and sulfates, and
   c. Phosphates and sulfates of lithium, aluminum and magnesium.

4. The method of producing biodiesel according to claim 2, wherein the porosity promoter is amylose-amylopectin (starch).

5. The method of producing biodiesel, according to claim 2, wherein the clays as binders are montmorillonite.

6. The method of producing biodiesel according to claim 2, wherein the catalyst has a surface area of 10 to 180 m$^2$/g, pore volume from 0.1 to 0.5 cm$^3$/g, and average pore diameter from 100 to 200 Å.

7. The method of producing biodiesel according to claim 1, wherein the transesterification of triglyceride esters with alcohols in a heterogeneous phase is carried out using vegetable oils selected from the group consisting of palm oil, jatropha, castor, soybean and sunflower, and a C$_1$-C$_4$ alcohol in an alcohol: oil ratio of 3:1 to 50:1.

8. The method of producing biodiesel according to claim 1, wherein the transesterification of triglyceride esters with alcohols in heterogeneous phase in batch reaction systems is carried out in stirred tank with residence times from 20 minutes to 20 h.

9. The method of producing biodiesel according to claim 1, wherein the transesterification of triglyceride esters with alcohols in a heterogeneous phase in continuous flow reaction systems is carried out in a packed reactor flow rate in descending or ascending mode, at a space velocity of 0.1 to 10 h$^{-1}$, a pressure of 25 to 100 kg/cm$^2$, a temperature of 150 to 300° C. and a methanol/oil molar ratio of 10 to 40.

10. The method of producing biodiesel, according to claim 1, wherein the transesterification of triglyceride esters with heterogeneous phase alcohols in continuous, ascending or descending flow is carried out in combination with other catalytic materials of a basic nature selected from the group consisting of magnesium oxides, aluminum oxides and sodium oxides to simultaneously promote the esterification and transesterification reactions.

11. The method of producing biodiesel according to claim 7, wherein the transesterification of triglyceride esters with alcohols in heterogeneous phase in batch reaction systems is performed in stirred tank with residence times of 20 minutes to 20 h.

12. The method of producing biodiesel according to claim 1, wherein the transesterification of triglyceride esters with heterogeneous phase alcohols is carried out in a continuous flow reactor in a descending or ascending manner at a space velocity of 0.1 to 10 h$^{-1}$, a pressure of 25 to 100 kg/cm$^2$, a temperature of 150 to 300° C. and a molar ratio of methanol/Oil from 10 to 40.

13. The method of claim 2, wherein said catalyst includes 0.1 to 3 weight % lithium and 0.3 to 10 weight % aluminum.

14. The method of claim 2, wherein said metal cation is selected from the group consisting of titanium, magnesium and silicon and where said metal cation is present in an amount of 0.2 to 30 weight % based on the weight of the catalyst.

15. The method of claim 2, wherein said porosity promoter is a polysaccharide.

16. The method of claim 2, wherein said binder is a clay in the amount of 3 to 15% weight %.

17. The method of claim 2, wherein the catalyst has a surface area of 30 to 80 m$^2$/g, a pore volume of 0.1 to 0.3 cm$^3$/g, and an average pore diameter of 110 to 170 Å.

18. A method of producing biodiesel, comprising the steps of:
   feeding a triglyceride ester and an alcohol to a reactor in the presence of a heterogeneous acid catalyst primarily of Lewis acid in nature, wherein said heterogeneous acid catalyst comprises mixed metal salts of lithium aluminium phosphates, lithium aluminum sulfates, and mixtures thereof in the reactor; and
   transesterifying the triglyceride in the presence of said catalyst at a temperature from 150 to 300° C., at a residence time from 20 minutes to 20 h, a space velocity from 0.1 to 10 h$^{-1}$, a pressure 25-100 kg/cm$^2$ (24.5-98.07 bar), alcohol/oil molar ratio of 10 to 40, and catalyst concentration of 0.001 to 20 weight % based on the triglyceride.

19. The method of claim 18, wherein said catalyst further comprises a cation selected from the group consisting of magnesium, titanium, zinc, zirconium, gallium, and silicon.

20. The method of claim 19, further comprising 0.05 wt % of an organic or inorganic porosity promoter, and 1-10 wt % of a binder selected from the group consisting of clays, kaolin and metal oxides of the formula MxOy, where M=Al, Mg, Sr, Zr or Ti, X=1 or 2 and y=2 or 3.

21. The method of claim 19, wherein said catalyst comprises said lithium in an amount of up to 5 wt %, and aluminum in an amount of up to 15 wt %, and said cation in an amount of up to 40 wt % based on the weight of the catalyst.

* * * * *